US012599712B2

(12) United States Patent
Locke

(10) Patent No.: US 12,599,712 B2
(45) Date of Patent: Apr. 14, 2026

(54) ELECTRO-MECHANICAL PUMP CONTROLLER FOR NEGATIVE-PRESSURE TREATMENT

(71) Applicant: Solventum Intellectual Properties Company, Maplewood, MN (US)

(72) Inventor: Christopher Brian Locke, Bournemouth (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 248 days.

(21) Appl. No.: 17/631,684

(22) PCT Filed: Aug. 3, 2020

(86) PCT No.: PCT/IB2020/057332
§ 371 (c)(1),
(2) Date: Jan. 31, 2022

(87) PCT Pub. No.: WO2021/024164
PCT Pub. Date: Feb. 11, 2021

(65) Prior Publication Data
US 2022/0273864 A1 Sep. 1, 2022

Related U.S. Application Data

(60) Provisional application No. 62/883,524, filed on Aug. 6, 2019.

(51) Int. Cl.
*A61M 1/00* (2006.01)

(52) U.S. Cl.
CPC .............. *A61M 1/68* (2021.05); *A61M 1/962* (2021.05); *A61M 1/98* (2021.05); *A61M 1/74* (2021.05);
(Continued)

(58) Field of Classification Search
CPC .......... A61M 1/68; A61M 1/962; A61M 1/98; A61M 1/913; A61M 1/74; A61M 2205/07; A61M 2205/3344
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| (Continued) | | | |

FOREIGN PATENT DOCUMENTS

| | | | |
|---|---|---|---|
| AU | 550575 B2 | 3/1986 | |
| AU | 745271 B2 | 3/2002 | |
| (Continued) | | | |

OTHER PUBLICATIONS

Louis C. Argenta, Md and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Rebecca E Eisenberg
*Assistant Examiner* — Kate Elizabeth Strachan

(57) ABSTRACT

An apparatus for negative-pressure treatment may include an enclosure having a variable volume compressible to a minimum volume, a port and an actuation surface. The apparatus may include a first one-way valve configured to allow fluid ingress to the enclosure, a second one-way valve configured to allow fluid egress from the enclosure, and an actuator configured to apply a compressive force to the actuation surface. The apparatus may further comprise a motor coupled to the actuator to apply and remove the compression force and having an operating parameter indicative of the variable volume. The apparatus may further comprise a controller coupled to the motor and configured to turn on the motor to engage the actuator to alternately apply
(Continued)

and remove the compressive force until the enclosure is compressed to the minimum volume and turn off the motor in response to the operating parameter indicating that the chamber is compressed to the minimum volume.

20 Claims, 10 Drawing Sheets

(52) U.S. Cl.
CPC ......... *A61M 1/913* (2021.05); *A61M 2205/07* (2013.01); *A61M 2205/3344* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,625,362 B2 * | 12/2009 | Boehringer | A61M 1/74 604/304 |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2008/0200905 A1 * | 8/2008 | Heaton | A61M 1/784 604/543 |
| 2008/0309702 A1 * | 12/2008 | Takahashi | B41J 29/38 347/29 |
| 2013/0304007 A1 * | 11/2013 | Toth | A61M 1/74 604/319 |
| 2014/0163491 A1 | 6/2014 | Schuessler et al. | |
| 2015/0080788 A1 | 3/2015 | Blott et al. | |
| 2015/0367045 A1 * | 12/2015 | Locke | A61M 1/732 604/319 |
| 2017/0100525 A1 * | 4/2017 | Heaton | A61M 1/684 |
| 2017/0319758 A1 * | 11/2017 | Eddy | A61M 1/67 |
| 2018/0169308 A1 | 6/2018 | Hu et al. | |
| 2019/0328982 A1 * | 10/2019 | Sarangapani | A61M 1/90 |
| 2020/0199852 A1 * | 6/2020 | Hyodo | E02F 9/2253 |
| 2021/0071615 A1 * | 3/2021 | Matsubara | F02D 41/10 |

(56) References Cited

U.S. PATENT DOCUMENTS

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0048164 A1 * | 3/1982 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, Md et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, Md., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion; PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, The Use of Hypermia in the Postoperative Treatment of Lesions of the Extremities and Thorax, Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56)　　　　　　　References Cited

OTHER PUBLICATIONS

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

International Search Report and Written Opinion Corresponding to Application No. PCT/IB2020/057332, mailed Oct. 21, 2020.

* cited by examiner

FROM FIG. 5A

A

520 — WAIT FOR TIME PERIOD ($t$)

525 — TURN ON MOTOR FOR ONE REVOLUTION

530 — MEASURE MOTOR CURRENT ($i$) AND/OR VELOCITY ($w$)

$i \leq i_0$ AND/OR $w \geq w_0$

540

NO

550 — TURN ON MOTOR

YES

THERAPY COMPLETE?

555

NO

YES

560 — TURN OFF SYSTEM

ELECTRO-MECHANICAL PUMP CONTROLLER FOR NEGATIVE-PRESSURE TREATMENT

CROSS-REFERENCE TO RELATED APPLICATIONS

This application claims the benefit of priority to U.S. Provisional Application No. 62/883,524, filed on Aug. 6, 2019, which is incorporated herein by reference in its entirety.

TECHNICAL FIELD

The invention set forth in the appended claims relates generally to tissue treatment systems and more particularly, but without limitation, to a pump for applying negative-pressure to dressings and methods of using the pump for negative-pressure treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for applying negative-pressure to a dressing are set forth in the appended claims. Illustrative embodiments are also provided to enable a person skilled in the art to make and use the claimed subject matter.

For example, in some embodiments, an apparatus for applying negative pressure may comprise an electro-mechanical pump, such as a bellows pump, which may be configured to achieve high or low flow rates. The apparatus may additionally include a tubing set that is separable from the pump in some examples. At least some portions of the pump may be fluidly isolated from the tubing set. At least some portions of the pump may be reusable, and some portions (such as the tubing set) may be disposable.

In some examples, a pump apparatus for providing negative-pressure treatment may comprise an enclosure having a chamber, a port, and an actuation surface, wherein the chamber has a variable volume compressible to a minimum volume. The apparatus may also comprise a first one-way valve configured to allow fluid ingress to the chamber and a second one-way valve configured to allow fluid egress from the chamber. The pump apparatus may further comprise an actuator configured to apply a compression force to the actuation surface and remove the compression force from the actuation surface. A motor may be coupled to the actuator to apply and remove the compression force and may have an operating parameter indicative of the variable volume such as, for example, an operating current or an angular velocity. The apparatus may further comprise a controller coupled to the motor and configured to turn on the motor to engage the actuator and alternately apply and remove the compression force from the actuation surface until the chamber is compressed to the minimum volume. The controller may be further configured to turn off the motor in response to the operating parameter indicating that the chamber is compressed to the minimum volume. For example, the controller may be configured to turn off the motor in response to the presence of a no-load current or a no-load angular velocity being detected by the controller.

In some examples, the actuator may be detachably coupled to or otherwise separable from the actuation surface. In some embodiments, the actuator may detach from the actuation surface after the successive application and removal of the compressive force when the chamber has been fully compressed to the minimum volume to provide a desired negative pressure to a dressing. The controller may be configured to turn off the motor when the actuator detaches from the actuation surface as indicated by the presence of a no-load current or a no-load angular velocity being detected by the controller. In some embodiments, the controller may be configured to turn on the motor to determine whether the operating current and/or the angular velocity of the motor is less than or equal to a minimum current value and/or greater than or equal to a maximum angular velocity. If true, the controller may be configured to turn off the motor. The controller may be configured further to turn the motor back on for a limited period of time to determine whether the operating current and/or the angular velocity of the motor is still less than or equal to a minimum current value and/or greater than or equal to a maximum angular velocity. If still true, the controller may be configured not to turn the motor back on, but continue checking. But if not still true, the controller may be configured to turn on the motor to return the negative pressure back to the desired target pressure for treatment.

In some example embodiments, the compressive force may be generated by a linear motion that may be provided by a linear actuator. In some other example embodiments, the compressive force may be generated by a rotational motion. In yet other example embodiments, the compressive force may be generated by a rotational motion converted into a linear motion. In some embodiments, the apparatus may further comprise a cylindrical cam having a working surface configured to engage the actuation surface of the enclosure to convert a rotational motion to a linear motion. In some embodiments, the cylindrical cam may be a face cam having a working surface having a wedge shape.

In some examples, the pump may include a geared motor configured to drive a linear actuator that compresses a bellows. When the bellows is compressed, contents of the bellows, which may be mostly air, can be expelled through a first one-way valve, such as a duckbill valve, to a vented bag. If the linear actuator is retracted, the bellows can decompress without the linear actuator's assistance. During decompression of the bellows, contents of a closed dressing, which may be mostly air, may be drawn out of the dressing and into the bellows through a second one-way valve, such as a duckbill valve. Compression and decompression of the bellows can continue until the bellows no longer decompresses. Once the bellows no longer decompresses, the closed dressing is at a preset vacuum level. The vacuum level of the bellows may be altered by varying the material and/or the wall thickness of the bellows, for example.

Objectives, advantages, and a preferred mode of making and using the claimed subject matter may be understood best by reference to the accompanying drawings in conjunction with the following detailed description of illustrative embodiments. In some embodiments, the bellows and the two one-way valves may be part of a disposable tubing portion that can be attached to a dressing and a vented bag. At least some parts of the pump may be reusable. The pump may be designed to reduce electronic costs, may be designed for different flow rates, may be manually operated, may eliminate a need for a rigid canister, may eliminate fluid ingress into the device, and can work on a constant force curve irrelevant of the vacuum load on the system so as to reduce power draw.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
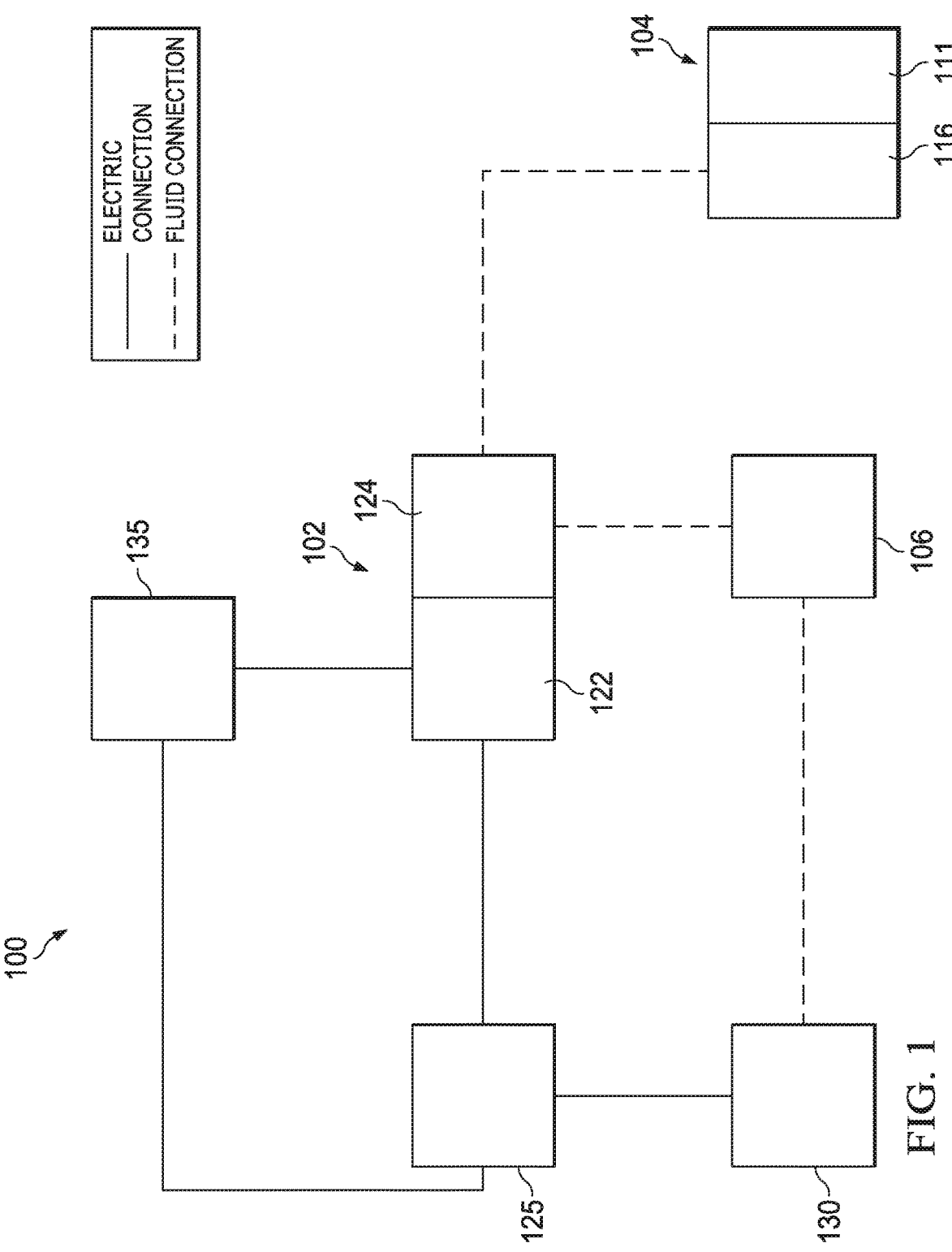
FIG. 1 is a functional block diagram of an example embodiment of a therapy system that can provide negative-pressure therapy in accordance with this specification.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

"Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

The therapy system 100 may include a source or supply of negative pressure, such as a negative-pressure source 102, and one or more distribution components. A distribution component is preferably detachable and may be disposable, reusable, or recyclable. A dressing, such as a dressing 104, and a fluid container, such as a container 106, are examples of distribution components that may be associated with some examples of the therapy system 100. One or distribution components, such as the dressing 104, may provide a fluid path between the negative-pressure source 102 and a tissue site. As illustrated in the example of FIG. 1, the dressing 104 may comprise or consist essentially of a tissue interface 114, a cover 116, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 104. For example, such a dressing interface may be a SENSA-T.R.A.C.™ Pad available from Kinetic Concepts, Inc. of San Antonio, Texas.

In general, components of the therapy system 100 may be coupled directly or indirectly. For example, the negative-pressure source 102 may be directly coupled to the container 106, and the container 106 may be indirectly coupled to the dressing 104 through the negative-pressure source 102. Coupling may include fluid, mechanical, thermal, electrical, or chemical coupling (such as a chemical bond), or some combination of coupling in some contexts. In some embodiments, components may also be coupled by virtue of physical proximity, being integral to a single structure, or being formed from the same piece of material. For example, the negative-pressure source 102 may be fluidly and mechanically coupled to the dressing 104 in some embodiments.

The container 106 is representative of a container, canister, pouch, bag, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The tissue interface 114 can be generally adapted to contact a tissue site. The tissue interface 114 may be partially or fully in contact with the tissue site. If the tissue site is a wound, for example, the tissue interface 114 may partially or completely fill the wound, or may be placed over the wound. The tissue interface 114 may take many forms, and may have many sizes, shapes, or thicknesses depending on a variety of factors, such as the type of treatment being implemented or the nature and size of a tissue site. For example, the size and shape of the tissue interface 114 may be adapted to the contours of deep and irregular shaped tissue sites. Moreover, any or all of the surfaces of the tissue interface 114 may have projections or an uneven, course, or jagged profile that can induce strains and stresses on a tissue site, which can promote granulation at the tissue site.

In some embodiments, the tissue interface 114 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the tissue interface 114 may be a foam having pore sizes in a range of 400-600 microns. The tensile strength of the tissue interface 114 may also vary according to needs of a prescribed therapy. For example, the tensile strength of a foam may be increased for instillation of topical treatment solutions. In one non-limiting example, the tissue interface 114 may be an open-cell, reticulated polyurethane foam such as GRANUFOAM™ dressing or V.A.C. VERAFLO™ dressing, both available from KCI of San Antonio, Texas.

The tissue interface 114 may be either hydrophobic or hydrophilic. In an example in which the tissue interface 114 may be hydrophilic, the tissue interface 114 may also wick fluid away from a tissue site, while continuing to distribute negative pressure to the tissue site. The wicking properties of the tissue interface 114 may draw fluid away from a tissue site by capillary flow or other wicking mechanisms. An example of a hydrophilic foam is a polyvinyl alcohol, open-cell foam such as V.A.C. WHITEFOAM™ dressing available from KCI of San Antonio, Texas Other hydrophilic foams may include those made from polyether. Other foams that may exhibit hydrophilic characteristics include hydrophobic foams that have been treated or coated to provide hydrophilicity.

The tissue interface 114 may further promote granulation at a tissue site when pressure within the sealed therapeutic environment is reduced. For example, any or all of the surfaces of the tissue interface 114 may have an uneven, coarse, or jagged profile that can induce microstrains and stresses at a tissue site if negative pressure is applied through the tissue interface 114.

In some embodiments, the tissue interface 114 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 114 may further serve as a scaffold for new cell-growth, or a scaffold material may be used in conjunction with the tissue interface 114 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 116 may provide a bacterial barrier and protection from physical trauma. The cover 116 may also be constructed from a material that can reduce evaporative losses and provide a fluid seal between two components or two environments, such as between a therapeutic environment and a local external environment. The cover 116 may comprise or consist of, for example, an elastomeric film or membrane that can provide a seal adequate to maintain a negative pressure at a tissue site for a given negative-pressure source. The cover 116 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38°

7                                                    8

C. and 10% relative humidity (RH). In some embodiments, an MVTR up to 5,000 grams per square meter per twenty-four hours may provide effective breathability and mechanical properties.

In some example embodiments, the cover 116 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 116 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 116 may comprise INSPIRE 2301 having an MVTR (upright cup technique) of 2600 $g/m^2/24$ hours and a thickness of about 30 microns.

An attachment device may be used to attach the cover 116 to an attachment surface, such as undamaged epidermis, a gasket, or another cover. The attachment device may take many forms. For example, an attachment device may be a medically-acceptable, pressure-sensitive adhesive configured to bond the cover 116 to epidermis around a tissue site. In some embodiments, for example, some or all of the cover 116 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

In operation, the tissue interface 114 may be placed within, over, on, or otherwise proximate to a tissue site. The cover 116 may be placed over the tissue interface 114 and sealed to an attachment surface near the tissue site. For example, the cover 116 may be sealed to undamaged epidermis peripheral to a tissue site. Thus, the dressing 104 can provide a sealed therapeutic environment proximate to a tissue site, substantially isolated from the external environment, and the negative-pressure source 102 can reduce the pressure in the sealed therapeutic environment. Negative pressure applied across the tissue site through the tissue interface 114 in the sealed therapeutic environment can induce macrostrain and micro-strain in the tissue site, as well as remove exudates and other fluids from the tissue site, which can be collected in container 106.

In some example embodiments of the therapy system 100, the negative-pressure source 102 may comprise an actuator unit 122 and a pump unit 124. In some example embodiments, the therapy system 100 may also comprise a controller 125 that may be operatively coupled to the actuator unit 122 and be configured to actuate the pump unit 124 to provide negative pressure to the dressing 104. The controller 125, actuator unit 122 and pump unit 124 may be packaged as a single unit or as separate components. For example, the actuator unit 122 and the controller 125 may be packaged as a single unit. Additionally, the therapy system 100 may include sensors to measure operating parameters and provide feedback signals to the controller 125 indicative of the operating parameters. For example, the therapy system 100 may include a first sensor 130 and a second sensor 135 coupled to the controller 125.

Sensors, such as the first sensor 130 and the second sensor 135, are generally known in the art as any apparatus operable to detect or measure a physical phenomenon or property, and generally provide a signal indicative of the phenomenon or property that is detected or measured. For example, the first sensor 130 and the second sensor 135 may be configured to measure one or more operating parameters of the therapy system 100. In some embodiments, the first sensor 130 may be a transducer configured to measure pressure in a pneumatic pathway and convert the measurement to a signal indicative of the pressure measured. In some embodiments, for example, the first sensor 130 may be a piezo-resistive strain gauge. The second sensor 135 may optionally measure operating parameters of the negative-pressure source 102, such as a voltage or current, in some embodiments. Preferably, the signals from the first sensor 130 and the second sensor 135 are suitable as an input signal to the controller 125, but some signal conditioning may be appropriate in some embodiments. For example, the signal may need to be filtered or amplified before it can be processed by the controller 125. Typically, the signal is an electrical signal, but may be represented in other forms, such as an optical signal.

In some embodiments, the controller 125 may receive and process data from one or more sensors, such as the first sensor 130. The controller 125 may also control the operation of one or more components of the therapy system 100 to manage the pressure delivered to the tissue interface 114. In some embodiments, controller 125 may include an input for receiving a desired target pressure and may be programmed for processing data relating to the setting and inputting of the target pressure to be applied to the tissue interface 114. In some example embodiments, the target pressure may be a fixed pressure value set by an operator as the target negative pressure desired for therapy at a tissue site and then provided as input to the controller 125. The target pressure may vary from tissue site to tissue site based on the type of tissue forming a tissue site, the type of injury or wound (if any), the medical condition of the patient, and the preference of the attending physician. After selecting a desired target pressure, the controller 125 can operate the negative-pressure source 102 in one or more control modes based on the target pressure and may receive feedback from one or more sensors to maintain the target pressure at the tissue interface 114.

In some embodiments, the controller 125 may have a continuous pressure mode, in which the negative-pressure source 102 is operated to provide a constant target negative pressure for the duration of treatment or until manually deactivated. Additionally or alternatively, the controller may have an intermittent pressure mode. For example, the controller 125 can operate the negative-pressure source 102 to cycle between a target pressure and atmospheric pressure. For example, the target pressure may be set at a value of −135 mmHg for a specified period of time (e.g., 5 min), followed by a specified period of time (e.g., 2 min) of deactivation. The cycle can be repeated by activating the negative-pressure source 102 which can form a square wave pattern between the target pressure and atmospheric pressure.

In some example embodiments, the increase in negative-pressure from ambient pressure to the target pressure may not be instantaneous. For example, the negative-pressure source 102 and the dressing 104 may have an initial rise time. The initial rise time may vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time may be a value substantially equal to the initial rise time.

In some example dynamic pressure control modes, the target pressure can vary with time. For example, the target pressure may vary in the form of a triangular waveform, varying between a negative pressure of 50 and 135 mmHg with a rise time set at a rate of +25 mmHg/min. and a descent time set at −25 mmHg/min. In other embodiments of the therapy system 100, the triangular waveform may vary between negative pressure of 25 and 135 mmHg with a rise time set at a rate of +30 mmHg/min and a descent time set at −30 mmHg/min.

In some embodiments, the controller 125 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 125, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figure 2:
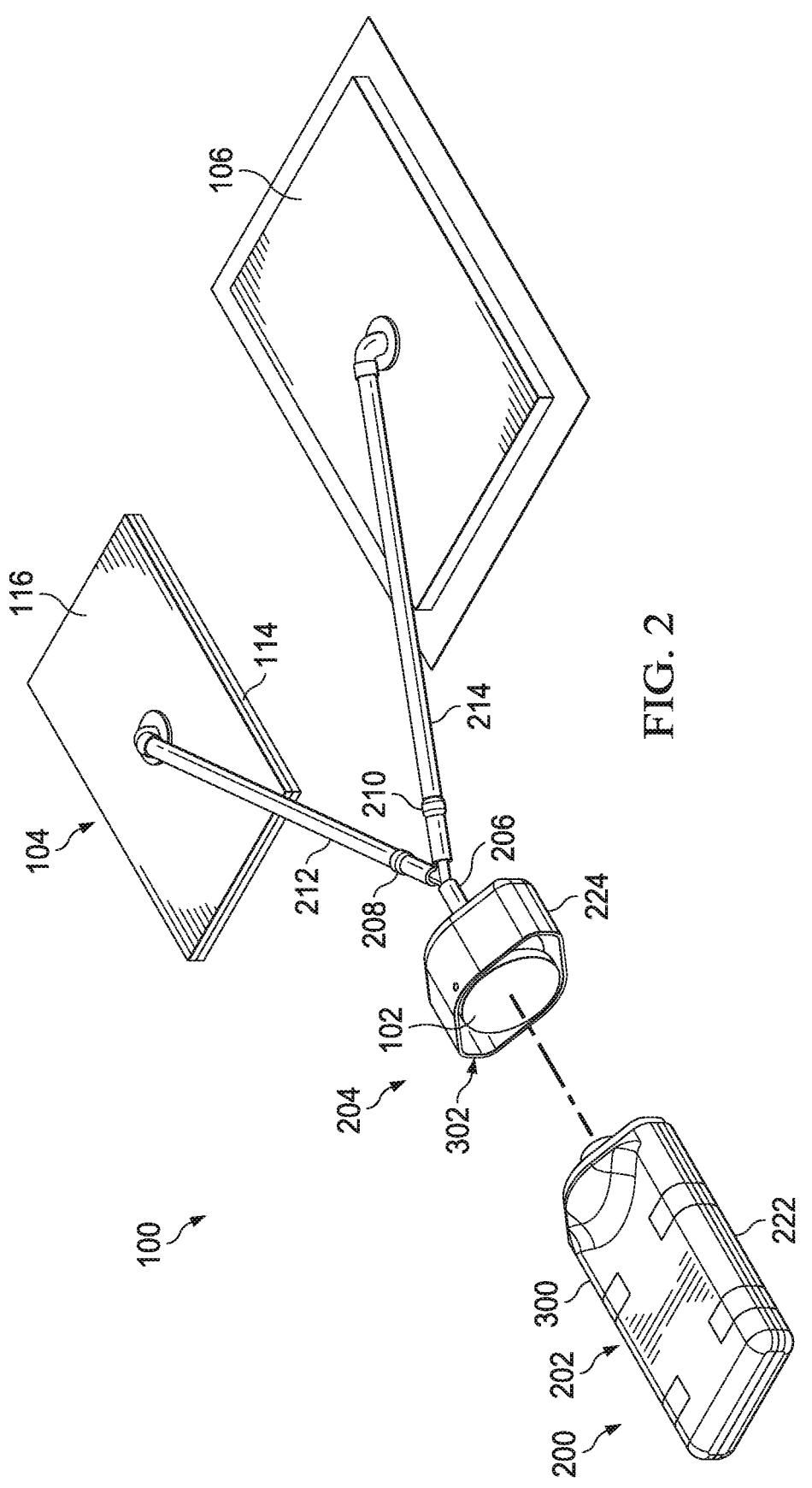
FIG. 2 is a schematic view of a first example of the therapy system of FIG. 1, illustrating additional details that may be associated with some embodiments.

FIG. 2 is a schematic diagram illustrating additional details that may be associated with some example embodiments of the therapy system 100. As illustrated in the example of FIG. 2, the therapy system 100 may include a therapy unit 200, which also may include an actuator unit 202 and a pump unit 204 in some embodiments similar to the actuator unit 122 and the pump unit 124. In some embodiments, the actuator unit 202, the pump unit 204, or both may be generally rectangular in shape, and may be sized and configured to be handheld. For example, one or both of the actuator unit 202 and the pump unit 204 may have various ergonomic features, such as curved edges and corners.

The pump unit 204 may comprise a port 206, which can be fluidly coupled to the dressing 104 through a first valve 208. The port 206 may also be fluidly coupled to the container 106 through a second valve 210. In some embodiments, the first valve 208 and the second valve 210 may be one-way valves. For example, one or more of the first valve 208 and the second valve 210 may be a duck-bill valve in some embodiments. A first fluid conductor, such as tubing 212, may fluidly couple the dressing 104 to the first valve 208. The container 106 may be in fluid communication with the second valve 210 via a second fluid conductor, such as tubing 214. In some embodiments, the container 106 may be a vented bag, as illustrated. Some embodiments of the actuator unit 202 may include an actuator housing 222, and the pump unit 204 may include a pump housing 224 and a pump 226. The pump 226 may be disposed within the pump housing 224 as shown in the example embodiment.

Figure 3:
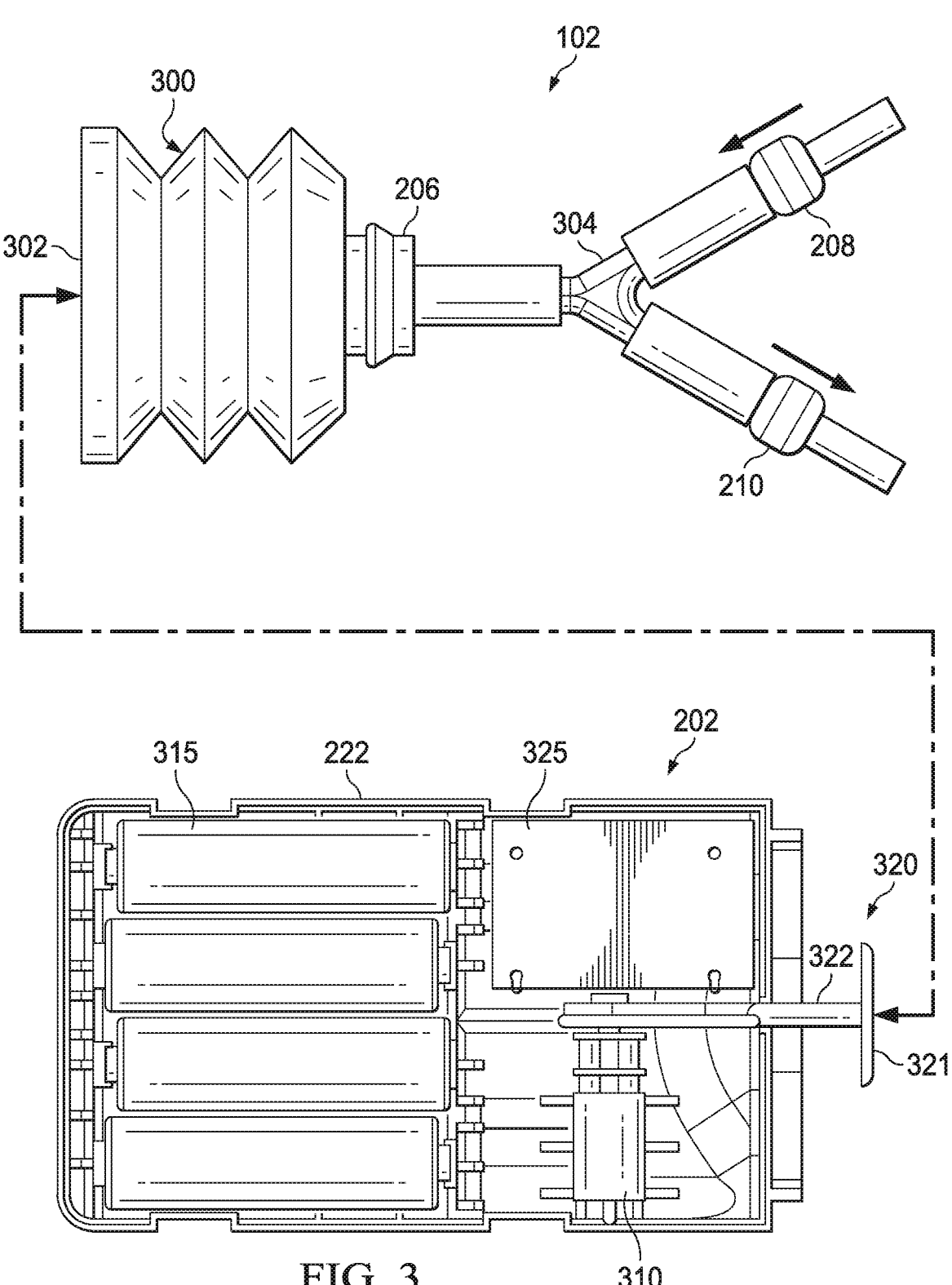
FIG. 3 is schematic view of a pump portion and an actuator portion of the therapy system of FIG. 2, illustrating additional details that may be associated with some embodiments.

FIG. 3 is schematic view of the actuator unit 202 and the pump 124 of the pump unit 204 as shown in FIG. 2, illustrating additional details that may be associated with some embodiments including how the actuator unit 202 may be coupled to the pump 226 of the pump unit 204. The pump 226 comprises or consists essentially of a chamber or other enclosure having a variable volume. For example the pump 226 may comprise an enclosure having a chamber and flexible sides, such as a bellows 300 with concertinaed sides. The bellows 300 may have an actuation surface 302 closing the chamber at a first end and a second end. In some embodiments, the bellows 300 may be fully expanded when no force is applied to the actuation surface 302, i.e., a relaxed state. The port 206 may be fluidly coupled to the second end of the bellows 300. A Y-connector 304 may fluidly couple the port 206 to the first valve 208 and the second valve 210.

The bellows 300 may be configured to generate a range of therapeutic negative pressure by varying the material or thickness of the flexible sides. In some examples, expansion of the bellows 300 can be configured to generate a negative pressure in a range of about 115 mmHg to about 135 mmHg. Moreover, a geometry of the bellows 300 may be chosen to maximize and/or increase a volume of the bellows 300 and/or a required or desired flow rate. For example, the flow rate is proportional to the volume of the bellows 300, which is proportional to the cross-sectional area and the height of the bellows 300. Consequently, the dimensions of the bellows 300 can be configured to generate a flow rate (for a given actuation rate) in a desired range.

The actuator unit 202 in some embodiments may include a circuit board 500, an actuator drive 310, a power supply 315, an actuator 320, and a circuit board 325 contained within the actuator housing 222. In some embodiments, the circuit board 325 may be configured to receive power from the power supply 315, which may comprise one or more small dry cell batteries. For example, standard AA batteries having an output voltage of 1.5 volts may be suitable for some configurations. The circuit board 325 may also comprise a drive circuit that may be configured to periodically operate the actuator drive 310 and to receive a voltage feedback signal from the actuator drive 310. The circuit board 325 may also comprise programmable circuitry and/or a logic circuit board with an on/off switch in some examples. The circuit board 325 may also comprise the controller 125 which may include a microprocessor, memory, inputs and outputs, and any of the foregoing devices on the circuit board 325.

In some embodiments, the actuator 320 may comprise an actuator surface 321 that may be configured to contact the actuation surface 302 as indicated by the dashed line to compress the bellows 300. The actuator 320 may further comprise and an actuator shaft 322 coupled between the actuator surface 321 and the actuator drive 310. In some examples, the actuator drive 310 may include an electric motor such as, for example, a DC motor powered by a fixed voltage source similar to the power supply 315 described above. The DC motor may be a gearmotor having a ratio of about 250:1 and a constant output speed of about 60 revolutions per minute may be particularly suitable for some embodiments. In the example embodiment shown, the gearmotor converts rotational motion to linear motion which motivates the actuator shaft 322 and the actuator surface 321 in a linear direction generally normal to the actuation surface 302.

The actuator 320 is configured to engage the actuation surface 302 if assembled as shown in the example of FIGS. 2 and 3. More particularly, the actuator surface 321 may be configured to engage the actuation surface 302 when drawing down negative pressure at the tissue site to a desired target pressure as described above. The controller 125 and other components on the circuit board 325 may be configured to periodically operate the actuator drive 310 which in turn linearly drives the actuator 320 to produce alternating extension and retraction strokes until the desired target pressure is reached. The actuator surface 321 may have a predetermined stroke length (SL) configured to disengage from the actuation surface 302 when the bellows 300 are fully compressed as a result of reaching the target pressure.

In an extension stroke, the actuator 320 can engage to the actuation surface 302 to apply a compression force. The compression force on the actuation surface 302 can be applied against the spring force of the bellows 300 to collapse the flexible sides of the bellows 300 which are normally expanded. Collapsing the flexible sides of the bellows 300 can decrease the volume of the bellows 300 and increase the pressure on any fluid in the bellows 300. Increased pressure on any fluid contents of the bellows 300 can expel the fluid contents through the port 206. The first valve 208 can prevent fluid flow through the tubing 212 to the dressing 104, and the increased pressure of the fluid in the bellows 300 can open the second valve 210 to allow fluid flow to the container 106. In some embodiments, the contents of the bellows 300 may include mainly air evacuated from the dressing 104.

In a retraction stroke, the actuator 320 is retracted from the actuation surface 302, removing the compression force from the actuation surface 302 of the bellows 300. Removing the compression force from the bellows 300 can allow the spring force of the flexible sides of the bellows 300 to expand the volume of the bellows 300. Notably, no external force may be required to expand the volume that results from the spring force of the bellows 300. The increased volume of the bellows 300 can decrease the pressure in the bellows 300, which can cause any fluid contents of the dressing 104 to be drawn through the first valve 208 into the bellows 300 thereby further reducing the negative pressure in the dressing 104. The bellows 300 in turn expelled the fluid contents to the container 106 during the following extension stroke as described above.

Figure 4A:
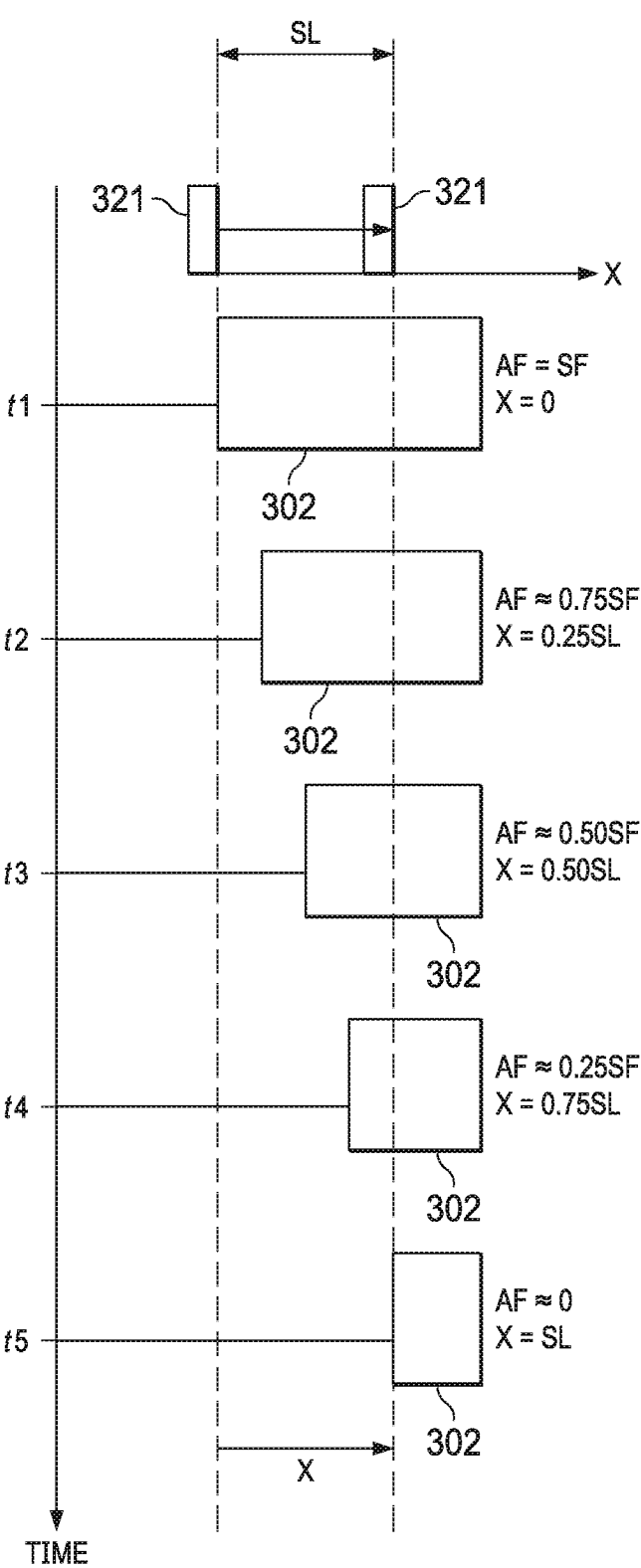
FIG. 4A is a graph of one example embodiment showing an amount of compressive force needed to be applied by an actuator that may be associated with the actuator portion of FIG. 3 against an actuation surface that may be associated with the pump portion of FIG. 3.

During successive retraction and extension strokes of the actuator 320, the bellows 300 may become more and more compressed as negative pressure builds up at the dressing 104 and overcomes the spring force or expansion force of the bellows 300. FIG. 4A is a graph of one example embodiment showing the amount of compressive force needed to be applied by the actuator 320 against the actuation surface 302 of the bellows 300 as they are compressed over time. More specifically, the actuator 320 can apply a compressive force, such as an actuator force (AF), that reduces over time as a result of an increase in negative pressure within the bellows 300 and the dressing 104 that overcomes the spring force (SF) of the bellows 300 as they are compressed from a relaxed position at time (t1) to a fully compressed position at time (t5). More specifically, when the actuator 320 compresses the actuation surface 302 of the bellows 300 by a displacement distance (x) in the amount of about 0.25 of the stroke length (SL) from time (t1) to time (t2), the amount of actuator force (AF) needed for the next extension stroke may diminish to about 0.75 of the spring force (SF). Correspondingly, when the actuator 320 compresses the actuation surface 302 of the bellows 300 by a total displacement distance (x) in the amount of about 0.50 of the stroke length (SL) from time (t2) to time (t3), the amount of actuator force (AF) needed for the next extension stroke may diminish to about 0.50 of the spring force (SF). When the actuator 320 compresses the actuation surface 302 of the bellows 300 by a total displacement distance (x) in the amount of about 0.75 of the stroke length (SL) from time (t3) to time (t4), the amount of actuator force (AF) needed for the next extension stroke may be only about 0.25 of the spring force (SF). And, when the actuator 320 compresses the actuation surface 302 of the bellows 300 to a fully compressed position wherein the total displacement distance (x) about equal to the stroke length (SL) from time (t4) to time (t5), the amount of actuator force (AF) needed for the next extension stroke may be close to zero because the actuation surface 302 may be configured to be decoupled from the actuator 320 as a result of being fully compressed.

Figure 4B:
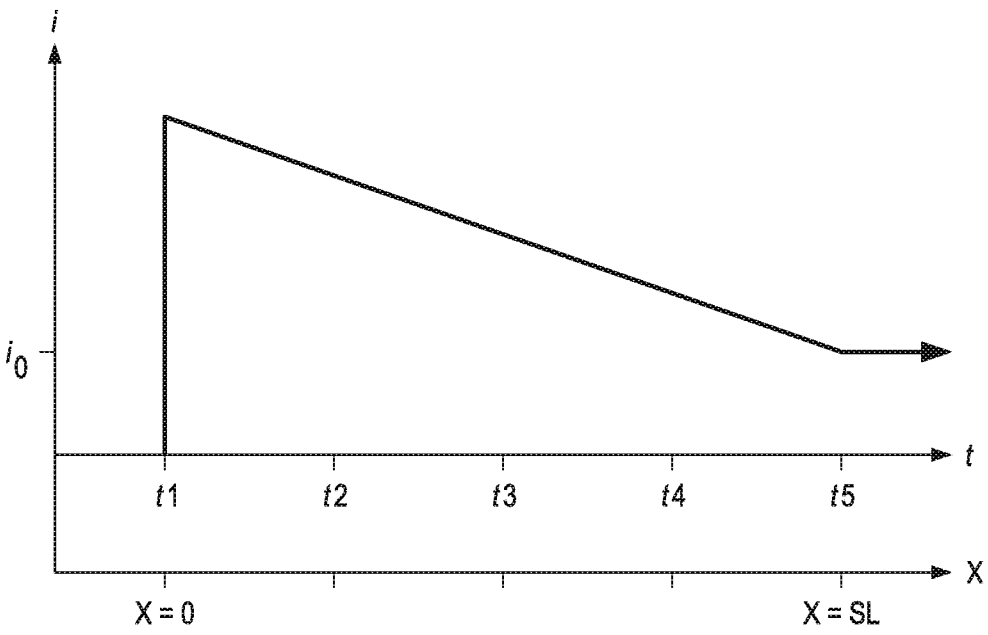
FIG. 4B is a graph of the example embodiment of FIG. 4A showing the amount of electrical current and/or angular velocity corresponding to the amount of compressive force needed to be applied by the actuator against the actuation surface.
Figure 4B:
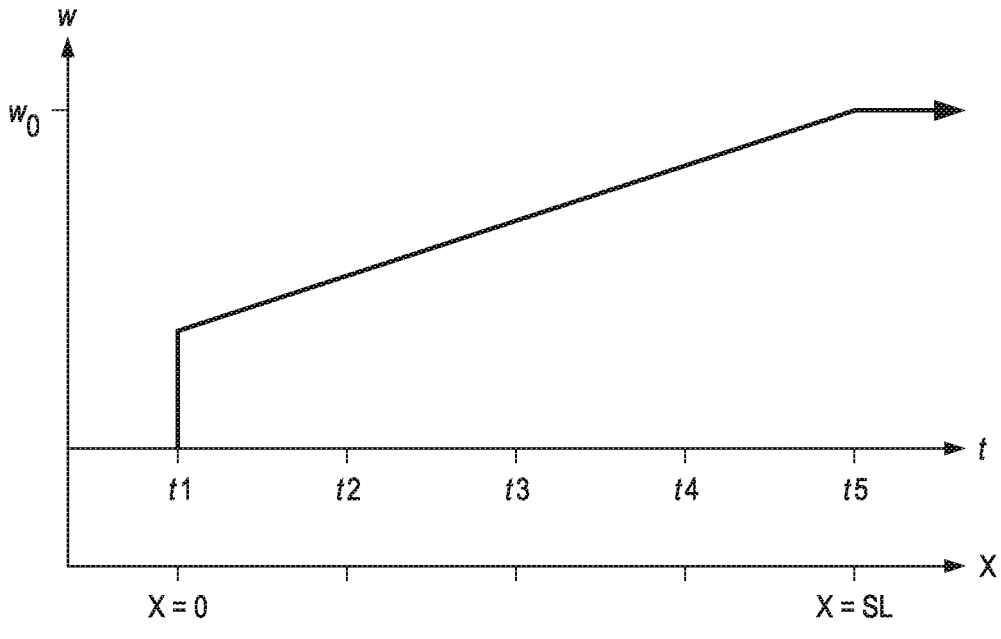

FIG. 4B is a graph of the example embodiment of FIG. 4A showing the amount of electrical current and/or angular velocity corresponding to the amount of compressive force needed to be applied by the actuator 320 against the actuation surface 302 of the bellows 300 as they are compressed over time. More specifically, the actuator 320 can apply an actuator force (AF) as described above that reduces over time as a result of an increase in negative pressure within the bellows 300 and the dressing 104 that overcomes the spring force (SF) of the bellows 300 as they are compressed from a relaxed position at time (t1) to a fully compressed position at time (t5). In some embodiments of the actuator 320 that included DC motor as described above, the DC motor would draw a higher current (i) needed by the actuator 320 to apply a higher actuator force (AF) at time (t1) than the DC motor would draw for the applicator 320 to apply a smaller actuator force (AF) at times (t2), (t3), or (t4) as shown. The DC motor eventually would draw a no-load current ($i_o$) at time (t5) when the actuator force (AF) is about zero as a result of the actuator 320 detaching or separating from the actuation surface 302. Similarly, the DC motor would operate at a lower angular velocity (w) as a result of the actuator 320 having to apply a greater actuator force (AF) at time (t1) to overcome the spring force (SF). As the spring force (SL) decreases, the applicator 320 would need to apply a decreasing actuator force (AF) at times (t2), (t3), or (t4) resulting in the angular velocity (w) increasing because of a smaller load on the DC motor. The DC motor eventually would be operating at a no-load angular velocity ($w_o$) at time (t5) as a result of the actuator 320 detaching or separating from the actuation surface 302.

After the bellows 300 are fully compressed and the negative pressure at the dressing 104 has been drawn down to the target pressure or within an acceptable range of the target pressure, the actuator 320 continues the successive retraction and extension strokes. Even if the actuator 320 is no longer coupled to the actuation surface 302, the DC motor is still drawing an electrical current such as, for example, the no-load current ($i_o$) at time (t5), to maintain the successive retraction and extension strokes of the actuator 320. In some embodiments of the actuator 320 that include a DC motor as described above, it would be desirable to turn off the motor completely to preserve battery power of the power supply 315. For example, it would be desirable to continuously measure the motor current (i) and compare it to a minimum current value or the no-load current ($i_o$) and/or continuously measure the motor angular velocity (w) and compare it to a maximum velocity value or the no-load angular velocity ($w_o$) to determine when the DC motor may be turned off in order to conserve battery power.

In some embodiments, the DC motor may be electrically coupled to the controller 125 that may be configured to measure the current drawn by the DC motor and/or the angular velocity at which the DC motor is operating. The controller 125 may be configured further to compare the current to the minimum current value or the no-load current ($i_o$) to determine when the chamber of the bellows 300 is fully compressed to the minimum volume for supplying the desired negative pressure, and then turning off the DC motor when the current is less than or equal to the minimum current value or the no-load current ($i_o$). Correspondingly, the controller 125 may be configured further to compare the angular velocity to the maximum velocity value or the no-load angular velocity ($w_o$) to determine when the chamber of the bellows 300 is fully compressed to the minimum volume for supplying the desired negative pressure, and then turning off the DC motor when the angular velocity is greater than or equal to the maximum velocity value or the no-load angular velocity ($w_o$). The controller 125 may be configured to turn off the DC motor based on either one, or both, of the minimum current value or the maximum velocity value.

Figure 5A:
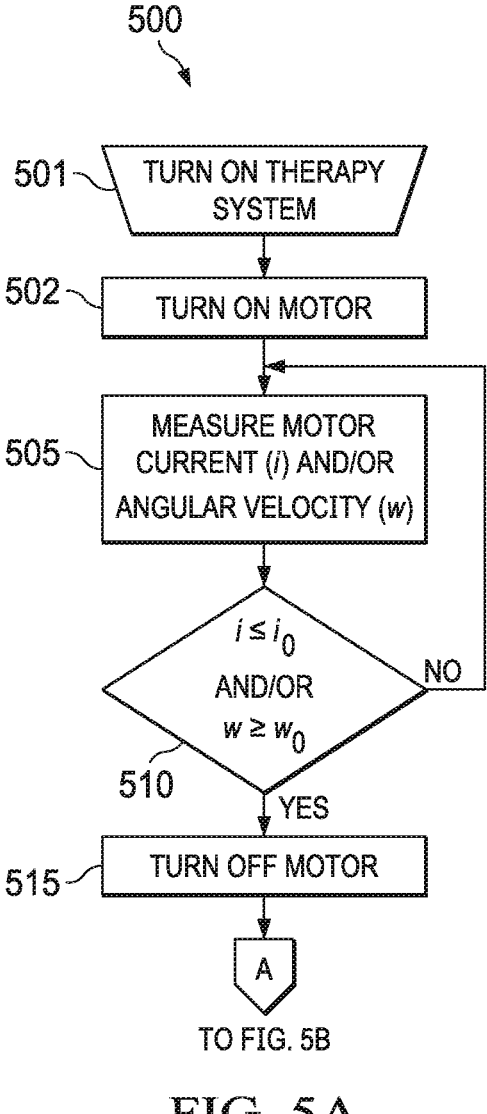
FIGS. 5A and 5B are flow charts illustrating a program for monitoring the electrical current and/or angular velocity of a motor that may be associated with the actuator portion of FIG. 3.
Figure 5B:
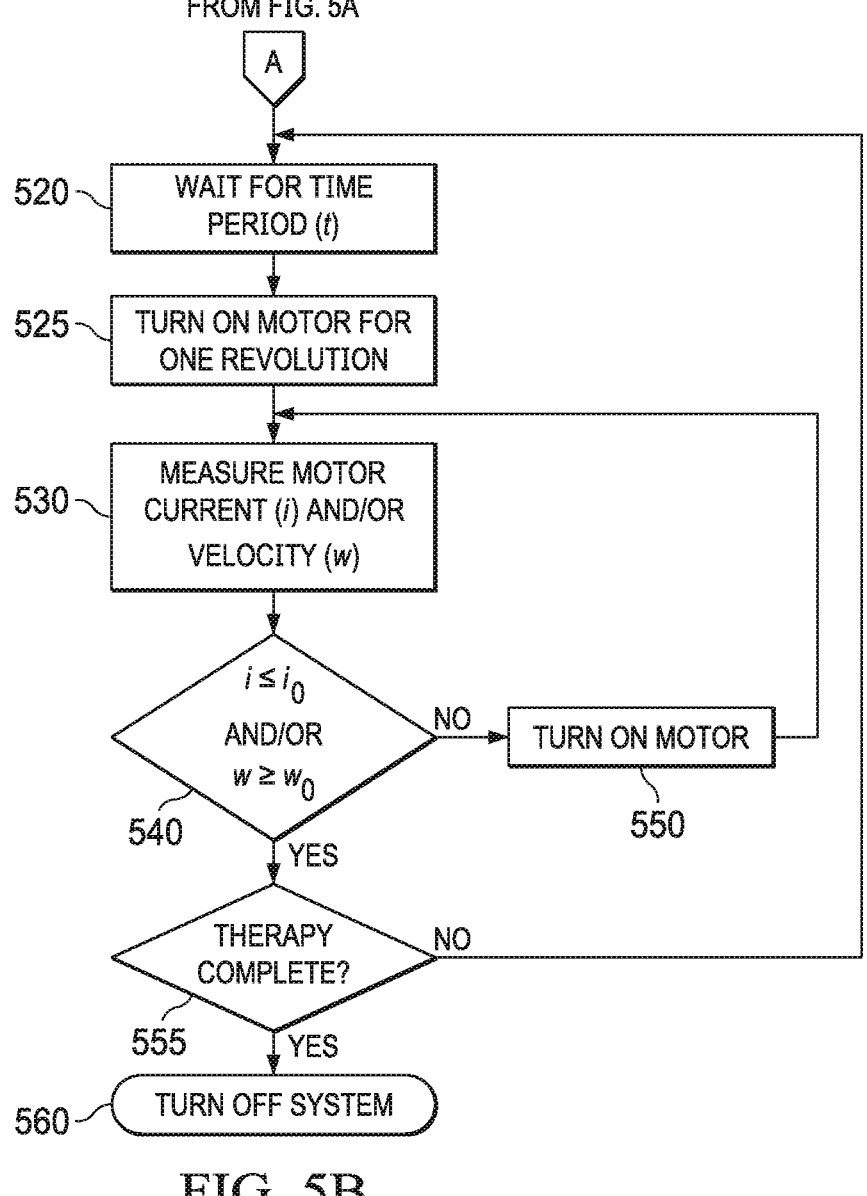

Referring to FIGS. 5A and 5B, flow charts illustrating a program 500 for monitoring the electrical current and/or angular velocity of a motor is shown that may be associated with the actuator unit 122 of FIG. 1 and, more specifically the actuator unit 202 of FIG. 3, for compressing the pump unit 124 to generate negative pressure as described above. More specifically, the corresponding controller 125 including the controller in the circuit board 325 may be configured to operate the program 500 in some example embodiments. A user or caregiver may commence therapy treatments by turning on the therapy system 501 and then turning on the motor at 502. The controller 125 may be configured to then measure the motor current (i) and/or the angular velocity (w) at 505. The controller 125 may be configured further to compare the motor current (i) measured to the minimum current value or the no-load current ($i_o$), and/or to compare the angular velocity (w) measured to the maximum velocity value or the no-load angular velocity ($w_o$) at 510 as described above in more detail. If the measured current (i) is not less than or equal to the minimum current value or the no-load current ($i_o$), i.e., NO, the program 500 returns to measuring the motor current (i) at 505. If the measured current (i) is less than or equal to the minimum current value or the no-load current ($i_o$), i.e., YES, the program 500 is configured turn off the motor at 515 as described above. Correspondingly, if the measured angular velocity ($w_o$) is not greater than or equal to the maximum velocity value or the no-load angular velocity ($w_o$), i.e., NO, the program 500 returns to measuring the angular velocity ($w_o$) at 505. If the measured angular velocity ($w_o$) is greater than or equal to the maximum velocity value or the no-load angular velocity ($w_o$), i.e., YES, the program 500 is configured turn off the motor at 515 as described above.

In some example embodiments, the program 500 may continue as shown from FIG. 5A to FIG. 5B wherein the program 500 is configured to determine when to turn back on the motor to compress the pump unit 124 in the event that the negative pressure drops below the desired target pressure. In one embodiment, for example, the controller 125 and the program 500 may be configured to wait for a predetermined deactivation time period (t) at 520 and then turned the motor back on again at 525 to again measure the motor current (i) and/or the angular velocity (w) at 530. In some embodiments, the program 500 may be configured to turn on the motor for a single revolution or a fixed number of revolutions sufficient for making the measurements without unduly draining the batteries. If the measured current (i) is not less than or equal to the minimum current value or the no-load current ($i_o$) at 540, i.e., NO, the program 500 may be configured to turn back on the motor at 550 to begin compressing the pump unit 124 to return the negative pressure to the desired target value. If the measured current (i) is less than or equal to the minimum current value or the no-load current ($i_o$), i.e., YES, the program 500 is configured to check if therapy is complete at 555. If therapy is not complete, the program may be configured to continue checking whether to restart the motor at 520. If therapy is complete, the program 500 may be configured to turn off the system at 560. Correspondingly, if the measured angular velocity ($w_o$) is not greater than or equal to the maximum velocity value or the no-load angular velocity ($w_o$) at 540, i.e., NO, the program 500 may be configured to turn back on the motor at 550 to begin compressing the pump unit 124 to return the negative pressure to the desired target value. If the measured angular velocity ($w_o$) is greater than or equal to the maximum velocity value or the no-load angular velocity ($w_o$) at 540, i.e., YES, the program 500 may be configured to check if therapy is complete at 555. If therapy is not complete, the program is configured to continue checking whether to restart the motor at 520. If therapy is complete, the program 500 may be configured to turn off the system at 560.

Figure 6:
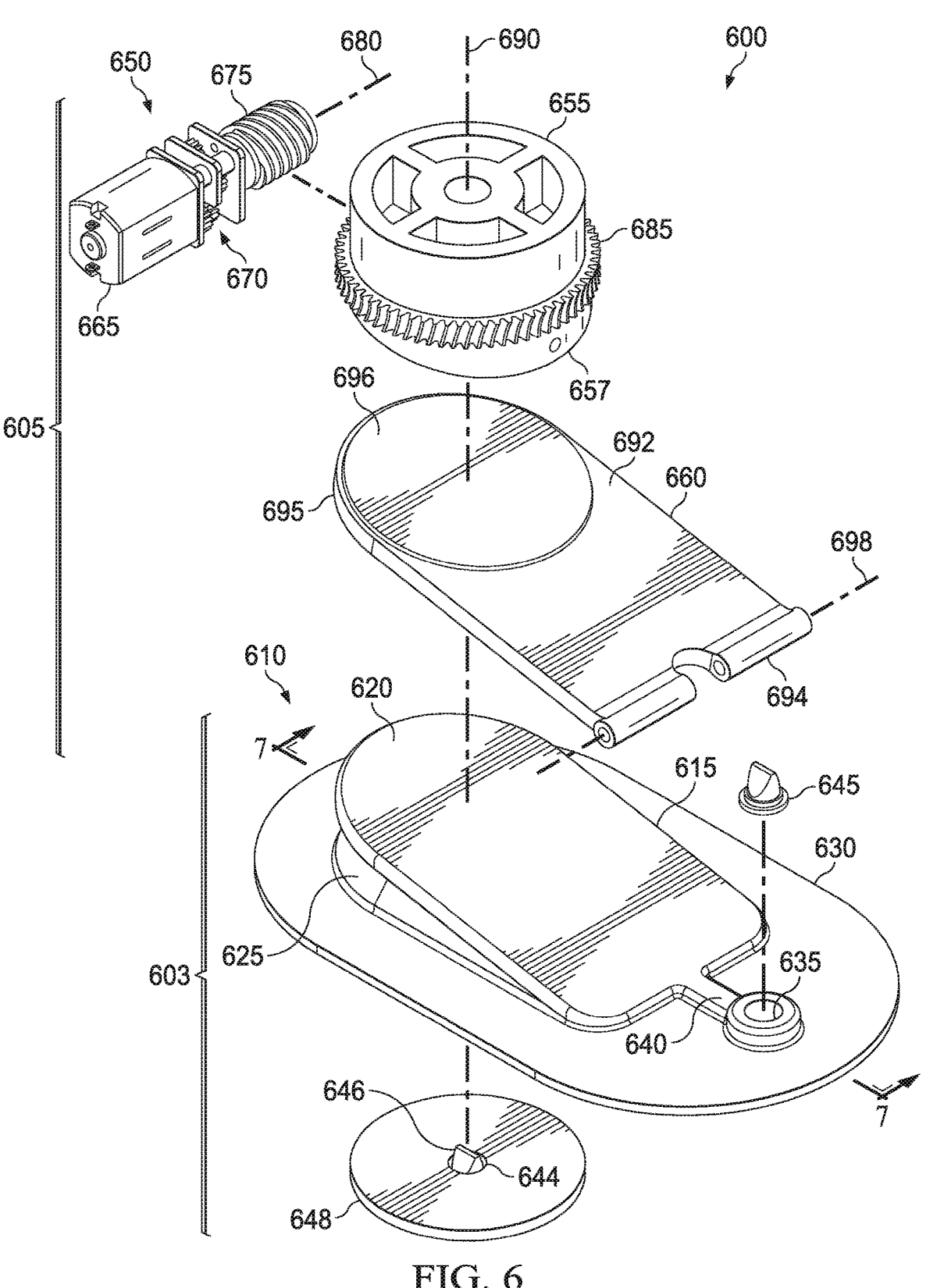
FIG. 6 is an exploded view illustrating additional details of a negative-pressure source that may be associated with some example embodiments of the therapy system of FIG. 1, illustrating additional details that may be associated with some embodiments.

FIG. 6 is an exploded view illustrating additional details of the negative-pressure source 102 as negative-pressure source 600 that may be associated with some example embodiments of the therapy system 100. In the example embodiment of FIG. 6, the negative-pressure source 600 may comprise a pump unit or pump 604 and an actuator unit or pump actuator 605 which in some embodiments is similar to the actuator unit 122 and the pump unit 124 of the negative-pressure source 102. In some embodiments, the pump 604 may be generally cylindrical in shape. In some other embodiments the pump 604 may be a generally wedge-shaped bellows pump as shown in FIG. 6.

As shown in the example embodiment of FIG. 6, the pump 603 may comprise a chamber assembly 610 having a chamber wall 615. The chamber wall 615 may include a drive surface 620 and a flexible wall 625 extending downward from the drive surface 620. In some embodiments, the drive surface 620 may have a rectangular shape having rounded corners at a first end and a semi-circle at a second end. In some embodiments, the flexible wall 625 may be concertinaed as shown in FIG. 6. In some embodiments, the flexible wall 625 may be corrugated. The chamber assembly 610 may further include a base 630 extending outward from the bottom of the chamber wall 615. The base 630 may extend around the entire perimeter of the bottom of the chamber wall 615. The base 630 may be configured to seal the chamber assembly 610 to the cover 116 (not shown). In some embodiments, the base 630 may include an egress or exhaust port 635 and an exhaust duct 640. The pump 603 may further include an exhaust valve 645 configured to be located in the exhaust port 635. The pump 603 may further include an ingress or intake port 644 and an intake valve 646 disposed within the intake port 644. In some embodiments, the intake valve 646 may be retained in a valve holder 648. In some embodiments, the pump 603 may be actuated by the pump actuator 605.

As further shown in FIG. 6, the pump actuator 605 may comprise a motor assembly 650, a cam 655 having an apex 656, and a drive plate 660. The motor assembly 650 may include a motor 665, a gear train 670, and a worm 675. The motor 665 may be an electric motor that is electrically coupled with and powered by a source of electrical energy, such as a battery. In some embodiments, the motor 665 may be a DC motor. The gear train 670 may be operatively coupled to the motor 665. The gear train 670 may comprise a plurality of gears to increase the torque of the motor 665. A driveshaft (not shown) may extend from the gear train 670. The worm 675 may be operatively coupled with the driveshaft such that the motor 665 can rotate the worm 675 about a worm axis 680. In some embodiments, the cam 655 may include a worm gear 685. In some embodiments, the cam 655 and the worm gear 685 may be integrally formed. The cam 655 may be configured to rotate about a cam axis of rotation 690. The worm gear 685 may be configured to be driven by the worm 675. Thus rotation of the motor 665 causes the worm 675 to rotate about the worm axis 680, which in turn engages the worm gear 685 to rotate the cam 655 and the apex 656.

In some embodiments, the drive plate 660 may comprise a plate 692 having a first end 694 and a second end 695. The first end 694 may be hinged and the second end 695 may be rounded. The plate 692 may be formed of a rigid material and may have a shape similar to that of the drive surface 620 of the chamber assembly 610. A slider disk 696 may be coupled to the plate 692 proximate the second end 695. The slider disk 696 may be circular in shape and may be formed of a rigid, low-friction material may be configured to function as an actuation surface for engaging the cam 655. The cam 655 may be a face cam having a generally cylindrical body and a working surface 657 on the face that may be wedged-shaped in some embodiments and configured to contact the slider disk 696. The low-friction material of the slider disk 696 may reduce the friction force on the cam 655, allowing the cam 655 to rotate more easily on the slider disk 696. Additionally, the first end 694 of the drive plate 660 may be rotationally coupled to a housing (not shown). The drive plate 660 may rotate about a hinge axis 698 during operation of the pump actuator 605. The drive plate 660 may be located between the cam 655 and the chamber assembly 610.

Cams are generally known by those skilled in the art to convert rotational motion to linear motion. As the worm 675 rotates the worm gear 685 and the apex 656 of the cam 655 around the cam axis of rotation 690, the apex 656 of the working surface 657 rotates into the slope of the slider disk 696 which provides a generally linear force against the slider disk 696, i.e., the actuation surface of the chamber assembly 610. When the cam 655 and the apex 656 have rotated 180° around the cam axis of rotation 690, the apex 656 rotates through an extension stroke to an extended position such that the apex 656 may displace the slider disk 696, i.e., the actuation surface, by a predetermined stroke length (SL). When the cam 655 is rotated by the worm 675 to the extended position, the apex 656 applies the linear force to the slider disk 696 to compress the chamber assembly 610 and force fluids into the container 106. When the cam 655 and the apex 656 have rotated from 180° to 360° to complete a rotation around the cam axis of rotation 690, the apex 656 rotates through a retraction stroke to a retracted position such that the apex 656 no longer displaces the slider disk 696 because the working surface 657 is again parallel to the slider disk 696. When the apex 656 to the retracted position, the linear force is removed from the slider disk 696 allowing the chamber assembly 610 to expand and continue drawing down additional negative pressure within the dressing 104.

Although not shown in FIG. 6, the components of the pump actuator 605 may be enclosed within a housing. The housing may operatively retain the motor assembly 650, the cam 655, and the drive plate 660. The motor 665 may be fixed within the housing. The cam 655 may be rotationally fixed within the housing such that the cam 655 can rotate about the cam axis of rotation 690. Additionally, the drive plate 660 may be rotationally fixed within the housing such that the drive plate 660 can rotate about the hinge axis 698.

Figure 7A:
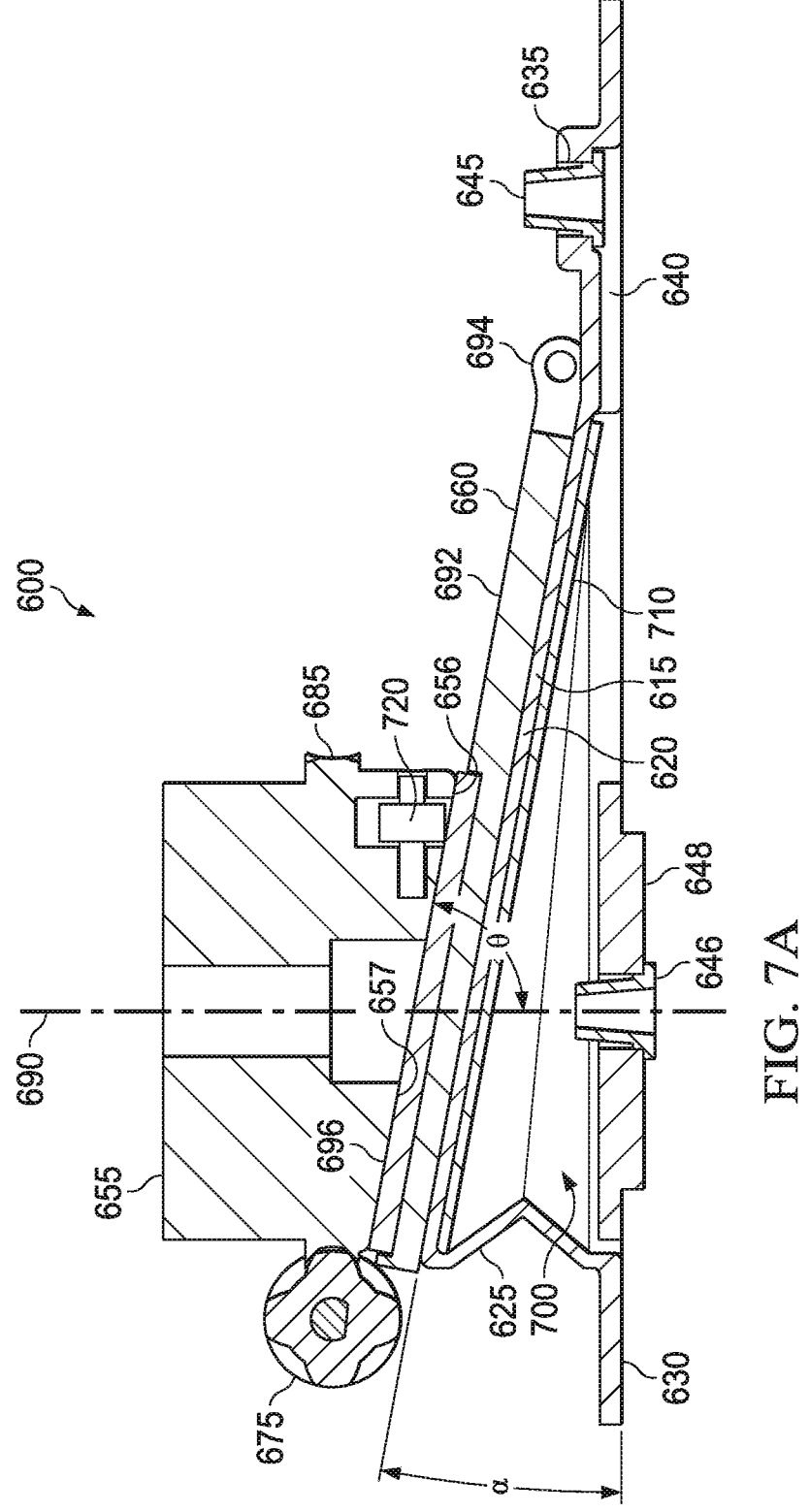
FIG. 7A is a section view of the negative-pressure source shown in FIG. 6, as assembled, taken along line 3-3, wherein the pump is shown in its retracted position.

FIG. 7A is a section view of the negative-pressure source 600 shown in FIG. 6, as assembled, taken along line 3-3, wherein the pump 603 is shown in its retracted position. As shown in FIG. 7A, the chamber wall 615 may define a pump chamber 700. In some embodiments, the drive surface 620 and the flexible wall 625 may define the pump chamber 700. The pump chamber 700 may be configured to be fluidly coupled to the tissue interface 114 (not shown) in the container 106 (not shown) in a fashion similar to that shown in FIG. 2. The exhaust duct 640 may fluidly couple the pump chamber 700 to the exhaust port 635 and the exhaust valve 645, which may be fluidly coupled to the container 106. The exhaust valve 645 may be configured to be located in the exhaust port 635. The exhaust valve 645 may only permit one-way fluid flow out of the pump chamber 700 into the container 106. In some embodiments, for example, the exhaust valve 645 may be a duckbill valve. The intake port 644 and the intake valve 646 may be configured to be fluidly coupled with the pump chamber 700 and may be fluidly coupled to the tissue interface 114. In some embodiments, the intake valve 646 may only permit one-way fluid flow from the tissue interface 114 into the pump chamber 700. In some embodiments, for example, the intake valve 646 may be a duckbill valve.

The pump 603 is in its retracted position when the working surface 657 is parallel to the slider disk 696. In the retracted position, the drive surface 620 may be oriented at a positive angle α with respect to the base 630. In some embodiments, in the retracted position, the drive surface 620 may be at an angle α in a range of about 10 degrees to about 45 degrees with respect to the base 630. In some embodiments, in the retracted position, the drive surface 620 may be at an angle α in a range of about 20 degrees to about 30 degrees with respect to the base 630. In other embodiments, in the retracted position, the drive surface 620 may at an angle α of about 30 degrees with respect to the base 630. In other embodiments, the drive surface 620 may at an angle α of about 15 degrees with respect to the base 630. As indicated above, the pump chamber 700 may have a wedge shape volume when viewed from the side as opposed to the generally cylindrical volume of the embodiment shown in FIG. 3.

In some embodiments, at least the flexible wall 625 of the chamber wall 615 may be formed of a resilient material. In some embodiments, for example, the drive surface 620, the flexible wall 625, and the base 630 may all be formed of a resilient material. In some embodiments, the drive surface 620, flexible wall 625, and base 630 may be integrally formed. In other embodiments, the drive surface 620 may be more rigid than the flexible wall 625. For example, the drive surface 620 may be substantially rigid such that it does not bend or yield during operation of the pump 603. In some embodiments, the pump 603 may further include a plate 710 coupled to the underside of the drive surface 620, within the pump chamber 700. The plate 710 may provide additional stiffness to the drive surface 620.

Additionally, the working surface 657 of the cam 655 may be characterize as an end cam or face cam. In some embodiments, the working surface 657 may be a wedge shape as shown. In some embodiments, the working surface 657 may be have a curved or arcuate surface for further reducing the friction between the slider disk 696 and the working surface 657. In some embodiments, the cam 655 may further include a roller bearing 720 located at the apex of the working surface 657. The roller bearing 720 may further reduce the friction force on the cam 655, allowing the cam 655 to rotate more easily on the slider disk 696. In some embodiments, the roller bearing 720 may extend slightly beyond the working surface 657.

When the cam 655 is in the retracted position, the working surface 657 of the cam 655 may have a positive angle that is equal to the positive angle of the drive surface 620 of the chamber assembly 610. Stated another way, when in the retracted position, the working surface 657 may be parallel to the drive surface 620 of the chamber assembly 610. In some embodiments, the working surface 657 may be at an angle θ in a range of about 45° to about 80° with respect to the cam axis of rotation 690. In some embodiments, the angle θ may be in a range of about 60° to about 70° with respect to the cam axis of rotation 690. In other embodiments, for example, the working surface 657 may be at an angle θ of about 60° with respect to the cam axis of rotation 690. In other embodiments, the working surface 657 may be at an angle θ of about 75° with respect to the cam axis of rotation 690.

Figure 7B:
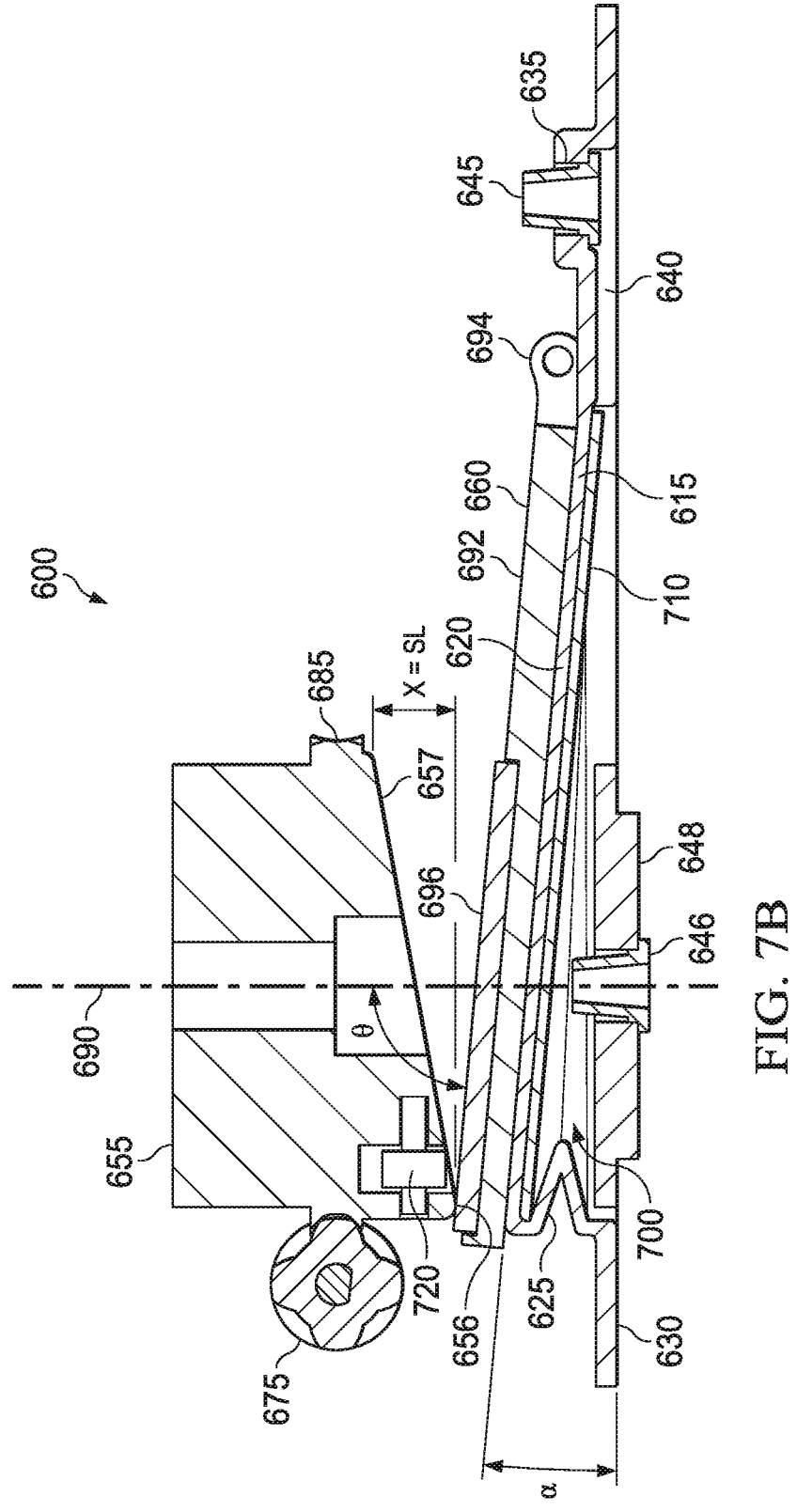
FIG. 7B is a section view of the negative-pressure source shown in FIG. 6, as assembled, taken along line 3-3, wherein the pump is shown in its extended position.

FIG. 7B is a section view of the negative-pressure source 600 shown in FIG. 6, as assembled, taken along line 3-3, wherein the pump 603 is shown in its extended position. In some embodiments, the apex 656 may be structured to have a predetermined height that provides a stroke length (SL) against the slider disk 696 as the cam 655 is rotated by the worm 675. As the cam 655 and the apex 656 rotate 180° from the retracted position, the apex 656 decreases the angle α between the drive surface 620 and the base 630 displacing the drive surface 620 and the slider disk 696, i.e., the actuation surface, by a displacement distance (x) that increases from zero to the stroke length (SL) before reaching the extended position. When the cam 655 is rotated by the worm 675 to the extended position, the apex 656 applies the linear force to the slider disk 696 to compress the pump chamber 700 to a minimum volume and force fluids into the container 106. Correspondingly, when the cam 655 and the apex 656 rotate from 180° to 360° to complete a rotation around the cam axis of rotation 690, the apex 656 rotates back to the retracted position allowing the angle α between the drive surface 620 and the base 630 to increase and reducing the displacement distance (x) from the full stroke length (SL) to zero before reaching the retracted position. When the cam 655 is rotated by the worm 675 from the extended position to the retracted position as shown in FIG. 7A, the working surface 657 is again parallel to the slider disk 696 thus removing the linear force from the slider disk 696 and allowing the pump chamber 700 to expand to a smaller volume as it continues to draw down additional negative pressure within the dressing 104.

During successive retraction and extension strokes of the apex 656, the pump chamber 700 may become more and more compressed as negative pressure builds up at the dressing 104 and overcomes the spring force or expansion force of the chamber assembly 610. The amount of compressive force needed to be applied by the apex 656 against the slider disk 696, i.e., the actuation surface, as the pump chamber 700 is compressed over time is similar to that shown in FIG. 4A. More specifically, the apex 656 can apply a compressive force, such as an actuator force (AF), that reduces over time as a result of an increase in negative pressure within the pump chamber 700 and the dressing 104 that overcomes the spring force (SF) of the chamber assembly 610 as the pump chamber 700 is compressed from a relaxed position at time (t1) to a fully compressed position at time (t5). More specifically, when the apex 656 compresses the chamber assembly 610 by a displacement distance (x) in the amount of about 0.25 of the stroke length (SL) from time (t1) to time (t2), the amount of actuator force (AF) needed for the next extension stroke may diminish to about 0.75 of the spring force (SF). Correspondingly, when the apex 656 compresses the chamber assembly 610 by a total displacement distance (x) in the amount of about 0.50 of the stroke length (SL) from time (t2) to time (t3), the amount of actuator force (AF) needed for the next extension stroke may diminish to about 0.50 of the spring force (SF). When the apex 656 compresses the chamber assembly 610 by a total displacement distance (x) in the amount of about 0.75 of the stroke length (SL) from time (t3) to time (t4), the amount of actuator force (AF) needed for the next extension stroke may be only about 0.25 of the spring force (SF). And, when the apex 656 compresses the chamber assembly 610 to a fully compressed position wherein the total displacement distance (x) about equal to the stroke length (SL) from time (t4) to time (t5), the amount of actuator force (AF) needed for the next extension stroke may be close to zero because the slider disk 696, i.e., the actuation surface, may be configured to be decoupled from the apex 656 as a result of being fully compressed.

Referring back to FIG. 4B, the graph again shows the amount of electrical current and/or angular velocity corresponding to the amount of compressive force needed to be applied by the apex 656 against the slider disk 696, i.e., the actuation surface, of the chamber assembly 610 as it is compressed over time. More specifically, the apex 656 can apply an actuator force (AF) as described above that reduces over time as a result of an increase in negative pressure within the pump chamber 700 and the dressing 104 that overcomes the spring force (SF) of the chamber assembly 610 as it is compressed from a relaxed position at time (t1) to a fully compressed position at time (t5). In some embodiments of the pump actuator 605 that includes a DC motor 665 as described above, the DC motor 665 would draw a higher current (i) needed by the apex 656 to apply a greater actuator force (AF) at time (t1) than the DC motor 665 would draw for the apex 656 to apply a smaller actuator force (AF) at times (t2), (t3), or (t4) as shown. The DC motor 665 eventually would draw a no-load current ($i_o$) at time (t5) when the actuator force (AF) is about zero as a result of the apex 656 detaching or separating from the slider disk 696, i.e., the actuation surface. Similarly, the DC motor 665 would operate at a lower angular velocity (w) as a result of the apex 656 having to apply a greater actuator force (AF) at time (t1) to overcome the spring force (SF) of the chamber assembly 610. As the spring force (SL) decreases, the apex 656 would apply a decreasing actuator force (AF) at times (t2), (t3), or (t4) resulting in the angular velocity (w) increasing because of a smaller load on the DC motor 665. The DC motor 665 eventually would be operating at a no-load angular velocity ($w_o$) at time (t5) as a result of the apex 656 separating from the slider disk 696, i.e., actuation surface.

After the pump chamber 700 is fully compressed and the negative pressure at the dressing 104 has been drawn down to the target pressure or within an acceptable range of the target pressure, the apex 656 continues the successive retraction and extension strokes as the cam 655 continues to rotate. Even if the apex 656 is no longer coupled to the slider disk 696, the DC motor 665 is still drawing an electrical current such as, for example, the no-load current ($i_o$) at time (t5), to maintain rotation of the cam 655 and the successive retraction and extension strokes of the apex 656. In some embodiments of the pump actuator 605, it would be desirable to turn off the motor completely to preserve battery power of the power supply (not shown) as described above. For example, it would be desirable to continuously measure the motor current (i) and compare it to a minimum current value or the no-load current ($i_o$) and/or continuously measure the motor angular velocity (w) and compare it to a maximum velocity value or the no-load angular velocity ($w_o$) to determine when the DC motor 665 may be turned off in order to conserve battery power.

In some embodiments, the DC motor 665 may be electrically coupled to the controller 125 that may be configured to measure the current drawn by the DC motor 665 and/or the angular velocity at which the DC motor 665 is operating. The controller 125 may be configured further to compare the current to the minimum current value or the no-load current ($i_o$) to determine when the chamber of the pump chamber 700 is fully compressed to the minimum volume for supplying the desired negative pressure, and then turning off the DC motor 665 when the current is less than or equal to the minimum current value or the no-load current ($i_o$). Correspondingly, the controller 125 may be configured further to compare the angular velocity to the maximum velocity value or the no-load angular velocity ($w_o$) to determine when the chamber of the pump chamber 700 is fully compressed to the minimum volume for supplying the desired negative pressure, and then turning off the DC motor 665 when the angular velocity is greater than or equal to the maximum velocity value or the no-load angular velocity ($w_o$). The controller 125 may be configured to turn off the DC motor 665 based on either one, or both, of the minimum current value or the maximum velocity value. Referring to FIGS. 5A and 5B, the program 500 for monitoring the electrical current and/or angular velocity of a motor may also be applicable to the controller 125 and the DC motor 665 as they are configured to commence compressing the pump chamber 700, turning off the DC motor 665 when the pump chamber 700 is fully compressed to provide the desired target pressure, and then turning back on the DC motor 665 to maintain the desired target pressure within the dressing 104.

The systems, apparatuses, and methods described herein may provide significant advantages. For example, in some embodiments, the actuator unit 202 is fluidly isolated from the pump unit 204 and may be decoupled from the pump unit 204. Since the actuator unit 202 can be fluidly isolated from the pump unit 204, decoupling the actuator unit 202 can allow the actuator unit 202 to be re-used. Additionally, a pump with a compressible chamber, such as the bellows 300, can be designed to stay compressed at a set vacuum level, which can eliminate the need for pressure transducers or other sensors. Further, because the contents of the dressing 104 can be expelled on compression, the container 106 may be an inexpensive vented bag in some embodiments. Additionally, the compression force may remain constant irrelevant of the vacuum level on the dressing 104 because fluid can be expelled to atmospheric pressure in some embodiments, which can also reduce power draw.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 106, or both may be eliminated or separated from other components for manufacture or sale. In other example configurations, the controller 125 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for negative-pressure treatment, the apparatus comprising:
   an enclosure having a chamber, a port and an actuation surface, the chamber having a variable volume compressible to a minimum volume;
   a first one-way valve configured to allow fluid ingress to the chamber through the port;
   a second one-way valve configured to allow fluid egress from the chamber through the port;
   an actuator configured to apply a compression force to the actuation surface and remove the compression force from the actuation surface;
   a motor coupled to the actuator to apply and remove the compression force and having an operating parameter indicative of the variable volume; and
   a controller coupled to the motor and configured to turn on the motor to engage the actuator to alternately apply and remove the compression force from the actuation surface until the chamber is compressed to the minimum volume, and turn off the motor in response to the operating parameter indicating that the chamber is compressed to the minimum volume;

wherein the operating parameter is current drawn by the motor as measured by the controller during operation; and wherein the current is a minimum current value when the chamber is compressed to the minimum volume.

2. The apparatus of claim 1, wherein the controller turns off the motor when the current is less than or equal to the minimum current value.

3. The apparatus of claim 1, wherein the operating parameter is the angular velocity of the motor as measured by the controller during operation and wherein the angular velocity is a maximum velocity value when the chamber is compressed to the minimum volume.

4. The apparatus of claim 3, wherein the controller turns off the motor when the angular velocity is greater than or equal to the maximum velocity value.

5. The apparatus of claim 1, wherein the compressive force is generated by a linear force.

6. The apparatus of claim 5, wherein the compressive force is applied by an extension stroke of the actuator.

7. The apparatus of claim 5, wherein the compression force is removed by a retraction stroke of the actuator.

8. The apparatus of claim 1, wherein the compression force is close to zero when the chamber is compressed to the minimum volume.

9. The apparatus of claim 1, further comprising a vented container fluidly coupled to the second one-way valve.

10. The apparatus of claim 1, further comprising a dressing fluidly coupled to the first one-way valve.

11. The apparatus of claim 1, wherein the motor is a DC motor.

12. The apparatus of claim 1, wherein the enclosure comprises flexible sides.

13. The apparatus of claim 1, wherein the enclosure comprises concertinaed sides.

14. The apparatus of claim 1, wherein the enclosure is a bellows.

15. The apparatus of claim 1, wherein the enclosure is generally cylindrically shaped.

16. The apparatus of claim 1, wherein the compressive force is generated by a rotational force.

17. The apparatus of claim 16, wherein the actuator comprises a cylindrical cam having a working surface configured to engage the actuation surface of the enclosure.

18. The apparatus of claim 17, wherein the cylindrical cam is an end cam.

19. A system for negative-pressure treatment, the system comprising:

a dressing;

an enclosure having a port and a variable volume compressible to a minimum volume;

a container fluidly coupled to the dressing through the enclosure;

a first one-way valve configured to allow fluid ingress to the enclosure from the dressing through the port;

a second one-way valve configured to allow fluid egress from the enclosure to the container through the port;

an actuator coupled to the enclosure to compress the enclosure to the minimum volume;

a DC motor coupled to the actuator and configured to draw a current for operating the actuator to compress the enclosure; and a controller coupled to the motor and configured to turn on the motor causing the actuator to compress the enclosure until the enclosure is compressed to the minimum volume, and turn off the motor in response to the current being less than or equal to a minimum current value.

20. A method of providing negative-pressure treatment to a tissue site, the method comprising:

placing a tissue interface proximate to the tissue site;

placing a cover over the tissue interface;

sealing the cover to an attachment surface peripheral to the tissue site;

fluidly coupling the tissue interface to a port of an enclosure having a variable volume;

fluidly coupling a container to the tissue interface through the port of the enclosure;

detachably coupling the enclosure to an actuator driven by a motor;

applying current to the motor to activate the actuator including:

extending the actuator to apply a linear force on the enclosure to compress the variable volume to expel fluid through the port into the container;

retracting the actuator to remove the linear force from the enclosure to allow the variable volume to expand and draw fluid from the tissue site into the enclosure through the port; and turning off the motor in response to the current being less than or equal to a minimum current value.

* * * * *